United States Patent [19]

Ebert et al.

[11] Patent Number: 4,601,908

[45] Date of Patent: Jul. 22, 1986

[54] PROCESS FOR THE PREPARATION OF PENICILLIN-FREE MYCELIUM MASSES FROM PENICILLIN PRODUCTION CULTURES FORMED BY FERMENTATION, AND THEIR USE AS ANIMAL FEEDS AND FERTILIZERS

[75] Inventors: Hildegard Ebert, Bad Soden am Taunus; Richard Kreutzfeldt, Frankfurt am Main, both of Fed. Rep. of Germany

[73] Assignee: Hoechst Aktiengesellschaft, Frankfurt, Fed. Rep. of Germany

[21] Appl. No.: 682,574

[22] Filed: Dec. 14, 1984

Related U.S. Application Data

[63] Continuation of Ser. No. 350,170, Feb. 19, 1982, abandoned.

[30] Foreign Application Priority Data

Feb. 23, 1981 [DE] Fed. Rep. of Germany ....... 3106649

[51] Int. Cl.$^4$ .............................................. A23K 1/00
[52] U.S. Cl. .................................... 426/52; 435/272; 435/801; 435/853; 71/25
[58] Field of Search .................. 426/2, 54, 60, 61, 52, 426/53, 623, 630, 635, 807; 435/255, 267, 272, 801, 853; 71/25

[56] References Cited

U.S. PATENT DOCUMENTS

| | | | |
|---|---|---|---|
| 1,693,611 | 12/1928 | Mabee | 426/54 X |
| 3,127,764 | 3/1965 | Biehl | 426/54 X |
| 3,865,951 | 2/1975 | Spicer et al. | 426/60 |
| 3,875,304 | 4/1975 | Hunt et al. | 426/54 X |
| 3,917,853 | 11/1975 | Greenshields | 426/60 |
| 3,928,642 | 12/1975 | Hubert et al. | 426/520 |

OTHER PUBLICATIONS

Ceillison, "Feeds and Feedings", Reston Publishing Co., (1980), pp. 436–437.
Kim et al., "Deficient Autolytic Enzyme Activity in Antibiotic Tolerant Lactobacilli", Chem. Abstract No. 96:214185v.
Singh et al., "A Note on the Influence of Penicillin Mycelium Waste on the Growth Rate of *Hariana Calves*", Chem. Abst. vol. 87, Abst. No. 21177z.
Ghosh et al., "Anaerobic Sludge Digestion in the Presence of Lactobacillus Additive", Symp. Pap. Energy Biomess Wastes 4, (1980), 295–317, cited in Chem. Abst. vol. 94:33537z.
Tarabrina et al., "Study of the Biological Properties of Antibiotic Resistant Strains of Lactic Acid Bacteria", Chem. Abstracts, vol. 91, (1979), Abst. No. 117899v.
Dutta et al., "Degradation of Macrolide-Lincosamide-Streptogramin Antibiotics by Lactobacillus Strains from Animals", Chem. Abst. vol. 95, (1981), 36241e.
Bayer et al., "Bacterial Synergy Between Penicillin or Ampicillin & Aminoglycosides Against Antibiotic Tolerant Lactobacilli", Chem. Abstr. vol. 93, (1980), 19958k.
Tarabrina et al., Zh. Mikrobiol, Epidemiol, Immunobiol., 1979, (7) 88–92.
Ehrhart et al., "Arzneimittel", vol. 4, Part 1, Verlag Chemie, Weinheim (1972), p. 204.

*Primary Examiner*—R. B. Penland
*Attorney, Agent, or Firm*—Curtis, Morris & Safford

[57] ABSTRACT

The invention relates to a process for the preparation of penicillin-free mycelium masses from water-containing penicillin production culture (=wet mycelium), which have been formed by fermentation, by removing the residual penicillin usually contained therein by subjecting the wet mycelium to anaerobic lactic fermentation using penicillin-resistant Lactobacilli, in which, with the mycelium mass being broken down, a penicillin-free silage product results, which can be stored under anerobic conditions and is used as animal feed, in particular for cattle and pigs, or as fertilizer.

10 Claims, No Drawings

PROCESS FOR THE PREPARATION OF PENICILLIN-FREE MYCELIUM MASSES FROM PENICILLIN PRODUCTION CULTURES FORMED BY FERMENTATION, AND THEIR USE AS ANIMAL FEEDS AND FERTILIZERS

This application is a continuation of application Ser. No. 350,170, filed Feb. 19, 1982, abandoned.

The present invention relates to a process for the preparation of penicillin-free mycelium masses in which penicillin residues are removed, by anerobic bacterial digestion under preserving ensilage conditions, from penicillin production cultures formed by fermentation, and to the use of the resulting silage product as an animal feed, in particular as a one-component feed for pigs and cattle, and as a fertilizer.

In the microbiological production of the antibiotic penicillin, large amounts of Penicillium mycelium are formed as a troublesome by-product during the fermentation. Penicillium mycelium is the fungus substance of the penicillin-forming agent *Penicillium chrysogenum*. It is separated off from the culture solution, for example by filtration or centrifugation, in the process for the production of penicillin, and still contains varying amounts of residual penicillin, depending on the effectiveness of the washing process used. The penicillin is found in the filtrate of the culture solution, and is isolated by extraction of the solution.

Disposal or utilization of the mycelium masses unavoidably obtained in these fermentation processes is particularly impeded by their residual penicillin content, harmless removal of which is an important prerequisite for most dumping or utilization possibilities. The amount of so-called wet mycelium mass, which is obtained with a water content of about 80-90% by weight and mostly in compact form, is about 25-35 tons per 100 $m^3$ of culture solution. It can be brought to about 25 to 30% by weight of dry mass by intensive subsequent pressing, for example on a belt press. The dry mass (=DM) has on average, for example, the following composition: 91% by weight of organic matter, of which 44% by weight is crude protein, and 9% by weight of inorganic matter, the residual penicillin content being about 2,000-5,000 mg/kg of DM.

Because of its high water content, the crude mycelium product obtained, which preferably contains about 10 to 30% by weight of dry mass, very readily decays. After only one day, it starts to turn into a foul-smelling mass as a result of the rapid onset of putrefaction. This means that the mycelium must be disposed of or put to a suitable use within a short period of time.

Previously, when microbiological production of penicillin took place on a relatively small scale, there were still practicable ways of disposing of the mycelium without great difficulty, for example by dumping on waste tips or supplying as animal feed. More recently, however, such disposal has no longer been possible. Dumping on waste tips is out of the question because of the very large amount of mycelium, for example about 30 tons daily, obtained in modern large-scale plants and the severe odor nuisance emanating therefrom. For environmental pollution reasons, the entire mycelium product must therefore be disposed of another way, for example by passing it in high dilution through a biological treatment plant; this procedure, however, is associated with enormous expenditure.

Utilization as animal feed is also not permitted today, because of the residual content of penicillin.

Because of its nitrogen content, attempts have already been made to employ the mycelium for fertilizing in agriculture. However, there are difficulties in finding sufficiently large areas which are available every day throughout the entire year. In this case also, an odor nuisance cannot be excluded, and when residual penicillin contents are still present, there is the danger of a possible development of resistance to penicillin in humans and animals.

German Democratic Republic Patent Specification 139,083 describes a process for the preparation of a penicillin-free mycelium dry product which can be used, for example, as fertilizer or animal feed, in which the aqueous mycelium suspension is acidified to a pH value of <5 and subjected to spray-drying at 150° to 300+ C., and the penicillin content is thereby destroyed.

U.S. Pat. No. 3,928,642 describes a process for destroying the residual penicillin by heating the mycelium masses to 140°-200° C. under pressure and subsequently drying them, and describes the use of the process product as animal feed.

Both processes, however, require expensive apparatus and high energy costs, and are highly uneconomical in practice.

The present invention was thus based on the object of freeing the mycelium masses obtained on a large industrial scale from their residual penicillin content in a simple and economical manner and of obtaining the mycelium product with its valuable protein content in a quality enabling as much as possible of it to be further utilized, for example as inexpensive animal feed, in particular in the fattening of productive livestock, or as fertilizer.

It has now been found, surprisingly, that the residual penicillin content in water-containing penicillin production cultures (=wet mycelium) formed by fermentation can be eliminated virtually completely if the penicillin crude mycelium masses which contain the usual amounts of residual penicillin, preferably about 2,000 to 5,000 mg of penicillin per kg of dry mass, are subjected to anaerobic lactic fermentation using penicillin-resistant Lactobacilli, in the course of which the mycelium mass is broken down and converted into a silage product.

It has also been found that Lactobacilli which are in themselves penicillin-sensitive can, for example, be acclimatized to penicillin by being cultured anaerobically in part amounts of the crude mycelium mass containing the usual amounts of residual penicillin, with the addition of sugar which can be converted into lactic acid by fermentation. They thereby degrade the residual penicillin by lactic fermentation, the mycelium mass being broken down and the tube-like mycelium structures being partly destroyed, and a penicillin-free mycelium silage product is obtained, which product contains lactic acid and has thereby become storable, contains penicillin-resistant Lactobacilli and is outstandingly suitable as an inoculum for penicillin-degrading, anaerobic lactic fermentation of further crude mycelium ensilage masses, in the course of which the formation of penicillin-resistant Lactobacilli continues.

Penicillin-resistant Lactobacilli can be obtained starting, for example, from those known bacterial lactic acid-forming agents such as are preferably present in large amounts in agricultural silages produced anaerobically by lactic fermentation, for example grass silages, green maize silages, beet leaf silages and the like, by using these silage products or the silage liquid as the Lactobacillus inoculum, or such as are also ubiquitous, usually in a sufficient amount, in the surrounding atmosphere, by leaving the crude mycelium part amount to be inoculated to stand in the open air for some hours, for example to store them openly as filter cake mass beside the filter press in the filtration plant.

The present invention thus relates to a process for the preparation of penicillin-free mycelium masses from water-containing penicillin production cultures (=wet mycelium) which are formed by fermentation and contain the usual amount of residual penicillin, with elimination of the residual penicillin, which comprises subjecting the Penicillium crude mycelium mass containing residual penicillin to anaerobic lactic fermentation using penicillin-resistant Lactobacilli.

As a variant of the above main process, a process is also claimed wherein anaorobic lactic fermentation is first carried out in a part of the Penicillium crude mycelium mass under conditions which are known per se, penicillin-resistant Lactobacilli being obtained and the crude mycelium mass being converted into a penicillin-free mycelium silage product, which part is then passed to the main portion of the crude mycelium mass as an inoculum, the mass being subjected to anaerobic lactic fermentation according to the main process.

According to the invention, the lactic fermentation leads to a significant liquefying of the originally compact crude mycelium starting material, forming a silage mass which can be pumped, and, as a result of the formation of the lactic acid, to a reduction in the pH value of the mass to values <4.5, preferably of 4.2 to 4.5 and in particular of 4.4, which results in a preserving effect on the usually ocher-colored mycelium silage product, which keeps the latter storable at normal temperature under anaerobic conditions, for example in a silo, for several months. The silage product prepared according to the invention has a pleasant, slightly sour odor with a yeasty aroma. It is readily eaten by animals, in particular productive livestock, preferably cattle and pigs for fattening, and, as a protein-rich feed constituent or as a one-component feed together with other energy-righ feeds, leads in particular to excellent fattening results. The mycelium silage product contains, inter alia, the aminoacids lysine, methionine and cysteine.

The invention thus also relates to feeds containing the penicillin-free mycelium silage product prepared according to the invention, and to their use as animal feeds, in particular as feeds for productive livestock, preferably as feeds for fattening cattle and pigs.

The invention furthermore also relates to a method of fattening cattle and pigs, which comprises feeding, in the usual manner, the animals for fattening with mixed feeds containing the penicillin-free mycelium silage product prepared according to the invention.

Since the penicillin-free mycelium silage products prepared according to the invention were hitherto neither known nor described, the present invention thus likewise relates to them as such.

Another advantageous useful property of penicillin-free mycelium silage products according to the invention is that, in particular because of their nitrogen content, they are employed as universally usable fertilizers which do not pollute the environment, for example in fruit-growing, horticulture and viticulture, in agriculture and forestry, and to increase desirable environmental vegetation. The liquid consistency and the ability of the products to be pumped can be of considerable advantage during application and distribution, inter alia in that they can also be transported, for example via pipelines, to slopes or greenhouses, and can be distributed over the soil via sprinklers.

The procedure according to the invention can be used for all known penicillin production mycelia which are formed by fermentation. Those from the production of penicillin G and V are preferred. The Penicillium mycelia from the production of penicillin G are particularly preferred.

As appropriate analyses have shown, even using the most sensitive investigation and detection methods, penicillin can no longer be detected in the mycelium silage products prepared according to the invention.

This result is all the more surprising, since the expert has known for a long time that lactic fermentations effected by Lactobacilli, especially, for example, various fermentations carried out in the dairy industry, can be virtually completely inhibited by penicillin (compare, for example, Max Schultz "Das grosse Molkereilexikon" ("The Large Dairy Dictionary"), Volkswirtschaftlicher Verlag Kempten, volume II, 4th edition (1965), page 895). Moreover, the economics of the process according to the invention are clearly superior to all the mycelia treatment processes disclosed hitherto.

The ensilage according to the invention can be carried out either batchwise, for example in fermenting casks or silos, or continuously, for example in silos, which can be cylindrical and charged from the top and from which the finished silage product is removed continuously or at certain intervals of time via a discharge device, which can be located in the floor section which, for example, narrows conically. The continuous procedure, which is preferred, necessitates a minimum residence time in the container, this time being determined by the time requirement for the course of the desired lactic fermentation under the particular process conditions maintained, such as, for example, temperature, sugar content, residual penicillin content and bacterial activity. In a 12 $m^3$ silo tower, for example, it can be about 6 days under favorable conditions at 20°–25° C. If the mycelium silage product obtained is subsequently to be stored, storage must take place under anerobic conditions and the storage temperature advantageously should not exceed normal temperature.

Products which are preferably used as sugars which can be converted into lactic acid by fermentation are those such as are also employed, for example, in agricultural ensilage of feed. These are, in particular, molasses from the production of sucrose or glucose (sugar content about 50% by weight), hexoses from potato starch or maize starch, glucose, lactose, sucroses, such as cane sugar or beet sugar, invert sugar and dextrose. It is also possible to use all other known sugars and sugar-containing waste products, for example dried sugar beet chips from which molasses is made, sugar mixtures and sugar syrup products and, where appropriate, derivatives thereof, if these can be converted into lactic acid by fermentation, or aqueous solutions or dilutions thereof. Molasses are particularly preferred.

The sugar content of the crude mycelium mass used for the anaerobic lactic fermentation is preferably about 5 to 10% by weight, relative to the crude mycelium dry mass, the content not having a critical upper limit and economic viewpoints generally being of prime importance in the choice thereof. In contrast, the lower limit of the sugar content cannot be lowered as far as desired. Rather, it must be of a minimum order of magnitude which permits lactic fermentation to an extent such that the resulting mycelium silage assumes a pH value of <4.5, from the lactic acid formed, and thereby becomes stable and storable. If the sugar contents are too low, there is the danger that too little lactic acid forms, that faulty fermentations may take place, for example with the formation of butyric acid and acetic acid, and that the residual penicillin content is not completely degraded, so that the silage decays and cannot be used for feeding. It has therefore proved advantageous for the crude mycelium mass employed preferably to contain at least 1.5% by weight, in particular 1.5 to 5% by weight, of sugar, relative to the total weight of water-containing crude mycelium mass (corresponding, for example, to about 3 to 10% by weight of molasses). It has furthermore been found that, advantageously, sugar nutrient contents which are as high as possible are made available to the bacteria, and in addition the sugar contents are within the upper part of the range given, during the first growing of penicillin-resistant Lactobacillus cultures which are later employed as inoculum. Preferably, 3.5 to 5% by weight of sugar, relative to the total weight of water-containing crude mycelium mass, or 25 to 35% by weight of sugar, relative to the crude mycelium dry mass, is employed.

The anaerobic lactic fermentation process according to the invention, with breakdown of mycelia, degradation of the residual penicillin and preserving acidification of the mycelium silage, proceeds at temperatures slightly below to slightly above the normal temperature, preferably at about 20° to 25° C. After fermentation has started, a pH value in the range from 4.5 to 4.2 can be achieved after only 2 to 3 days under advantageous fermentation conditions, the acid product remaining storable for some months under anaerobic conditions and at normal temperature. for example in a silo. However, a total fermentation time of at least 6 days is required, even under advantageous fermentation conditions, in order to be able to achieve complete degradation of the residual penicillin.

As can easily be seen under the microscope, the mycelium ensilage according to the invention proceeds with partial destruction of the tube-like mycelium structures. As a result of this breaking down of the mycelium, compared with the crude starting mycelium, the silage product is more easily digestible in the animal feed, is more readily consumed by animals and thus can be better utilized as feed.

It has also been found that it is possible also to add to the crude mycelium mass employed portions of those silable feed constituents such as are employed in the usual production of silage, for example grass, green maize, beet leaves, beet chips and, in particular, cereal straw, preferably in well-chopped form, in order to achieve, if necessary, the ability of the resulting mycelium silage product to be pumped. The amount of such feed constituents added is not in itself critical. Where appropriate, it is preferably up to at most 15% by weight, relative to the total weight of water-containing crude mycelium mass, if the silage product to be formed is to be obtained in pumpable form.

Feeding experiments on pigs and cattle have shown that these animals readily eat the mycelium silage product according to the invention, cattle sometimes requiring a short initial acclimatization phase. The cattle in the experiment also exhibited somewhat better weight increases than the control group. The product is very readily digested.

Mycelium silage products according to the invention are particularly preferably used as inexpensive, protein-rich one-component feeds together with other customary energy-rich feeds and, if appropriate, supplementary feeds in the fattening of pigs and cattle, it being possible to achieve excellent fattening results.

The invention is illustrated in more detail by the examples which follow, but without being limited thereto.

COMPARISON EXAMPLE 1

1 kg of Penicillium wet mycelium (compact) from the production of penicillin G (DM=11% by weight, penicillin G content=2,350 mg/kg of DM) was mixed with 30 g of sterile starch sugar solution (glucose content=50% by weight) under sterile conditions, without foreign infection, and the mixture was left to stand in a sterile 2 l conical flask at room temperature (23° C.) under anaerobic conditions, the residual oxygen in the flask being removed by covering the contents with a layer of nitrogen. A rubber stopper with a small fermentation tube filled with distilled water served as the seal for the flask.

After 7 days, the lactic acid content and residual penicillin content of the material in the flask were investigated.

The penicillin was determined by an agar diffusion test, combined with a penicillinase test.

It was found that no lactic fermentation or formation of lactic acid had taken place, and also that the residual penicillin content had not been substantially reduced.

COMPARISON EXAMPLE 2

1 kg of penicillium wet mycelium (compact) from the production of penicillin G (DM=10% by weight, penicillin G content=2,520 mg/kg of DM) was mixed with 30 g of sterile starch sugar solution (glucose content=50% by weight) and 100 g of set milk (as Lactobacillus inoculum) under sterile conditions without foreign infection and the mixture was left to stand for 7 days in a sterile 2 l conical flask at room temperature (23° C.) under anaerobic conditions analogously to Comparison Example 1. The lactic acid content and residual penicillin content of the material in the flask were then investigated. It was found that no lactic fermentation or formation of lactic acid had taken place and also that the residual penicillin content had not been substantially reduced. This meant that the Lactobacilli in the soured set milk could not effect lactic fermentation in the wet mycelium mass containing residual penicillin.

The dry masses (=DM) of the penicillium wet mycelia employed in Comparison Examples 1 and 2 had the following composition: 91% by weight of organic matter, of which 44% by weight was raw protein, and 9% by weight of inorganic substance, residual penicillin G content=2,350 and 2,520 mg/kg of DM.

EXAMPLE 1

0.5 kg of penicillium wet mycelium (compact) from the production of penicillin G (DM=18% by weight, comprising 91% by weight of organic matter and 9% by weight of inorganic matter, penicillin G content=2,060 mg/kg of DM, pH value=5.6) was mixed with 50 g of starch sugar solution (glucose content=50% by weight) and 0.5 kg of moist green maize silage and the mixture was introduced into a 2 l conical flask. The residual oxygen in the flask was removed by covering the contents with a layer of nitrogen, and the flask was closed with a rubber stopper with a fermentation tube filled with distilled water. After the contents of the flask had been left to stand at 23° C. under anaerobic conditions for 12 days, their lactic acid content, residual penicillin content and pH value were investigated.

The determination of penicillin was carried out by an agar diffusion test, combined with a penicillinase test. The pH value was determined by means of a glass electrode. The lactic acid content was determined by titrimetry. Analysis after ensilage for 12 days: pH value of the silage product=4.4; lactic acid content of the silage product=3.6% by weight; and residual content of penicillin G (relative to the mycelium dry mass employed)=not detectable (=<0.05 mg/kg of mycelium DM).

The resulting ocher-colored silage product had a liquid consistency. It had an acid odor with a pleasantly yeasty aroma, contained penicillin-resistant Lactobacilli and was used as the Lactobacillus inoculum for new crude mycelium silation batches. The bacteria titer determined by counting was $10^7$-$10^8$ Lactobacillus germs/g of moist silage product.

EXAMPLE 2

2 kg of penicillium wet mycelium (compact) from the production of penicillin G (DM=15% by weight, comprising 91% by weight of organic matter and 9% by weight of inorganic matter, penicillin G content=4,000 mg/kg of DM, pH value=5.9) were spread in a thickness of about 5 cm on a filter cloth at the end of the harvesting line of the penicillin fermentation tank and were left to stand in the atmosphere in the treatment plant in this form for 2 hours for the purpose of Lactobacillus infection.

1 kg of this Penicillium wet mycelium which had been bacterially infected in the atmosphere and had the above characteristics was mixed with 100 g of starch sugar solution (glucose content=50% by weight) and the mixture was left to stand in a conical flask under anaerobic conditions for 18 days, as described in Example 1, whereupon ensilage took place. The contents of the flask were investigated as described in Example 1.

Analysis after 18 days ensilage: pH value of the silage product=4.3; lactic acid content of the silage product=4.2% by weight; residual content of penicillin G (based on the mycelium dry mass employed)=not detectable (=<0.05 mg/kg of mycelium dry mass).

The resulting ocher-colored silage product had a liquid consistency. It had an acid odor with a pleasantly yeasty aroma, contained penicillin-resistant Lactobacilli, a large number of which were visible under the microscope, and was used as the Lactobacillus inoculum for new crude mycelium silation batches.

The bacteria titer was 1 to $5.10^8$ Lactobacillus germs/g of moist silage product.

EXAMPLE 3

Silation in a 12 m³ cylindrical silation tower made of plastic (GFK material), ϕ1 m, narrows conically in the floor section with a discharge device, closed to entry from air at the top by a loosely fitting cover plate.

10,000 kg of Penicillium wet mycelium (compact) from the production of penicillin G (DM=15.5% by weight, comprising 91% by weight of organic matter and 9% by weight of inorganic matter, penicillin G content=3,500 mg/kg of DM, pH value=5.6)+300 kg of molasses (sugar content=50% by weight)+400 kg of inoculum silage containing penicillin-resistant Lactobacilli and prepared according to Example 1 were introduced into the silation tower in alternate layers, and the tower was closed with a loosely fitting lid. The ensilage period was 7 days at 20°-25° C. The silage product was investigated as described in Example 1.

Analysis after 7 days ensilage: pH value of the silage product=4.4; lactic acid content of the silage product=2.7% by weight; residual content of penicillin G (based on the mycelium dry mass employed)=not detectable (=<0.05 mg/kg of mycelium dry mass).

The resulting ocher-colored silage product had a liquid consistency and could be pumped. It had an acid odor with a pleasantly yeasty aroma and contained penicillin-resistant Lactobacilli, a large number of which were visible under a microscope. The relatively low lactic acid content corresponded to the also relatively low sugar content which had been added to the crude mycelium mass employed.

The silage product was readily storable under customary anerobic conditions.

EXAMPLE 4

Silation in a 12 m³ silo corresponding to Example 3.

In order to increase the dry mass content of the starting wet mycelium, the latter was dehydrated further by subsequent pressing on a Winkler belt press, and was ensilaged with the resulting higher DM content as follows: 10,000 kg of subsequently pressed Penicillium wet mycelium (compact) from the production of penicillin G (DM=26.5% by weight, comprising 91% by weight of organic matter and 9% by weight of inorganic matter, penicillin G content=2,800 mg/kg of DM, pH value=5.8)+300 kg of molasses (sugar content=50% by weight)+1,000 kg of inoculum silage containing penicillin-resistant Lactobacilli and prepared according to Example 3 were introduced in alternate layers into the silo and were ensilaged at 20°-25° C. for 7 days, as described in Example 3, and the silage product was investigated.

Analysis after 7 days silation: pH value of the silage product=4.5; lactic acid content in the silage product=3.0% by weight; residual content of penicillin G (based on the mycelium dry mass employed)=not detectable (=<0.05 mg/kg of mycelium DM).

The resulting silage product had virtually the same appearance and analogous properties to the silage product described in Example 3. It was liquid and pumpable.

EXAMPLE 5

It was also possible to carry out the ensilage, described in Examples 3 and 4, in the silo continuously. About 2 m³ per day of finished silage were taken from the bottom of the silo filled with silage product and 2 m³ per day of fresh crude mycelium with added molasses+10% by weight of inoculum silage containing penicillin-resistant Lactobacilli were introduced at the top. The silage removed from the bottom was used as the inoculum silage. The minimum residence time of the ensilaged mycelium mass in the silo at about 20° to 25° C. was about 6 days. The continuously obtained silage product had analogous properties to the silage products described in Examples 3 and 4 and was also completely free from residual contents of penicillin G.

We claim:

1. A method for removing residual penicillin from a crude mass of Penicillin mycelium, formed by fermentation in the production of penicillin and containing water and residual penicillin, which method comprises adding to the crude mass at least 1.5 percent by weight of said crude mass of a sugar, convertible to lactic acid by penicillin resistant Lactobacilli and then anaerobically fermenting said mass containing about 2000 to 5000 milligrams of penicillin per kilogram of the dry weight of said crude mass with penicillin resistant Lactobacilli to produce a fermented silage product, said penicilllin resistant Lactobacilli being obtained by adapting naturally occurring penicillin-sensitive Lactobacilli in the presence of Penicillin mycelium.

2. A method as in claim 1 wherein agricultural silage, which has been fermented in the presence of Penicillin mycelium, is introduced as a pencillin-resistant Lactobacillus inoculum into said crude mass.

3. A method as in claim 2 wherein said agricultural silage is maize silage.

4. A method as in claim 1 wherein the penicillin resistant Lactobacilli used are obtained by allowing a part of the Penicillin mycelium to stand open in the atmosphere for several hours.

5. A method as in claim 1 wherein said crude mass has a dry solids content of 10 to 30 percent by weight, the balance being water.

6. A method as in claim 1 wherein said crude mass is formed by fermentation in the production of penicillin G.

7. A method as in claim 1 wherein said crude mass is pressed prior to anaerobically fermenting.

8. A method as in claim 1 wherein agricultural silage or unfermented ensiable material, is added to said crude mass prior to fermenting.

9. A method as in claim 1 wherein said crude mass comprises 1.5 to 5 percent by weight of added sugar convertible to lactic acid by said Lactobacilli.

10. A method as in claim 1 wherein said sugar is molasses.

* * * * *